United States Patent [19]

Kidwell et al.

[11] 4,151,186
[45] Apr. 24, 1979

[54] PREPARATION OF ACYL CHLORIDES

[75] Inventors: Roger L. Kidwell, Des Peres; Gary J. Lynch, St. Louis, both of Mo.

[73] Assignee: Monsanto Company, St. Louis, Mo.

[21] Appl. No.: 880,683

[22] Filed: Feb. 23, 1978

[51] Int. Cl.² ............................................. C07F 7/00
[52] U.S. Cl. .......................... 269/429.3; 260/429 CY; 260/544 L; 260/544 Y
[58] Field of Search ............ 260/429.3, 544 L, 544 Y, 260/429 CY

[56] References Cited

U.S. PATENT DOCUMENTS

| | | | |
|---|---|---|---|
| 2,818,416 | 12/1957 | Brown et al. | 260/429.3 X |
| 2,911,424 | 11/1959 | Kaufman | 260/429.3 |
| 2,983,740 | 5/1961 | Thomas et al. | 260/429.3 |
| 3,080,305 | 3/1963 | Gorsich | 260/429 CY X |
| 3,576,860 | 4/1971 | Lazaris | 260/544 Y |

OTHER PUBLICATIONS

Schwartz et al., Angew. Chem. Int. Ed. Engl., vol. 15 (6), pp. 333–340 (1976).
Bertelo et al., JACS 97, pp. 228–230 (1975).
Hart et al., JACS 97, pp. 679–680 (1975).
Hart et al., JACS 96, pp. 8115–8116 (1974).

*Primary Examiner*—Helen M. S. Sneed
*Attorney, Agent, or Firm*—S. M. Tarter; E. P. Grattan; F. D. Shearin

[57] ABSTRACT

A process which comprises contacting a zirconium compound having the formula

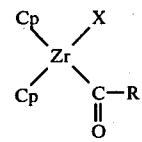

wherein
Cp is a π-cyclopentadienyl radical and each Cp can be the same or different,
X is an essentially non-interfering monovalent entity, and
R is alkyl or cycloalkyl, either of which may be unsubstituted or substituted, provided that the sterically least hindered position of R is bonded to C=O in the formula, with chlorine in the substantial absence of light to form

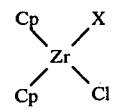

and

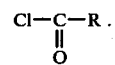

10 Claims, No Drawings

PREPARATION OF ACYL CHLORIDES

BACKGROUND OF THE INVENTION

1. Field of the Invention

This invention relates to organic synthesis, and more particularly to the use of certain organo zirconium complexes to functionalize olefins.

2. Description of the Prior Art

It has recently been discovered that zirconium chlorohydrides having the formula

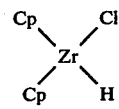

wherein Cp is an unsubstituted π-cyclopentadienyl radical, are useful in functionalizing, at a selective position, a variety of unsaturated organic molecules. Particularly related to this invention is the use of these zirconium compounds for selective functionalization of olefins, which is defined herein as the insertion of a radical in the olefin at a particular position with an accompanying elimination of the olefin double bond.

It has been reported that the above-identified zirconium chlorohydride reacts with the olefin rapidly under mild conditions (e.g., 25°–40° C. in benzene) to produce a di(π-cyclopentadienyl)(chloro)alkyl zirconium complex in which the zirconium is bound to the alkyl moiety at a position corresponding to the sterically least hindered position of the olefin as a whole. Reaction of the thus formed alkyl zirconium complex with an electrophilic reagent such as $Br_2$, $I_2$ or $C_6H_6ICl_2$ results in cleavage of the Zr-alkyl bond and formation of the corresponding halogenated alkane. Alternatively, procedures are described for first inserting a C=O radical into the Zr-alkyl bond of the alkyl zirconium complex and then using a similar electrophilic reagent to cleave the Zr-acyl bond and prepare an alkane having an acyl halide substituent. These procedures have been found to be particularly useful in preparing α-substituted alkanes from internal olefins. Illustrations of such uses of a di(π-cyclopentadienyl) zirconium chlorohydride have been published by J. Schwartz and others in J. Amer. Chem. Soc. at 96, 8115–16 (1974) and 97, 228–30 and 679–80 (1975) and in Angew. Chem. Int. Ed. Engl. at 15, No. 6, 333–40 (1976).

In the above-described procedure, various electrophilic reagents disclosed as useful in the step to cleave the Zr-alkyl or Zr-acyl bond are complex and expensive compounds and thus have questionable commercial economics. N-bromo-succinimide, N-chloro-succinimide and iodobenzene dichloride are examples of such compounds. It is desirable, therefore, to provide new and more economical methods to carry out this cleavage step. It is the primary object of the present invention to provide a new and improved method for cleavage of the Zr-acyl bond in the above-described process.

Further objects, aspects and advantages of this invention will be apparent from the description and claims which follow.

SUMMARY OF THE INVENTION

This invention provides a process for obtaining acyl chlorides by contacting a zirconium compound having the formula

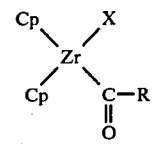

wherein
- Cp is a π-cyclopentadienyl radical and each Cp can be the same or different,
- X is an essentially non-interfering monovalent entity, and
- R is alkyl or cycloalkyl, either of which may be unsubstituted or substituted, provided that the sterically least hindered position of R is bonded to C=O in the formula, with chlorine in the substantial absence of light. The reaction of this process proceeds as follows:

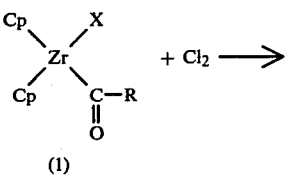

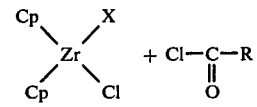

wherein Cp, R and X have the same meaning as described above. The acyl chloride and zirconium chloride can then be recovered from the resulting mixture.

DESCRIPTION OF THE PREFERRED EMBODIMENTS

In the various zirconium compounds employed in this invention, the radicals represented by Cp are in general any π-cyclopentadienyl radicals which are directly linked to the Zr atom and which do not substantially interfere with the desired reaction in the process of this invention. The two radicals bonded to the zirconium atom and represented by Cp can be the same or different. Typical, but not limiting examples of radicals which may be represented by Cp include a π-cyclopentadienyl radical that is unsubstituted (i.e., devoid of ring substituents other than hydrogen) and substituted π-cyclopentadienyl radicals such as a π-indenyl, π-fluorenyl, tetrahydro-π-indenyl, octahydro-π-fluorenyl, pentamethyl-π-cyclopentadienyl, pentaethyl-π-cyclopentadienyl, heptamethyl-π-indenyl, nonamethyl-π-fluorenyl or undecamethyltetrahydro-π-indenyl radical. Any of such radicals can be differently or further substituted (e.g., with other normal alkyl or cycloalkyl groups, with branched alkyl groups or with alkoxy or phenoxy groups) provided such substituents do not substantially interfere with the reactions desired in the process of this invention.

Certain of such substituents may advantageously increase the solubility of the zirconium compound in the particular reaction mass employed in the process of this invention, and a considerable amount of such substitution may be present in some cases. Where there is alkyl substitution of the ring(s) of such radicals it is typical for each alkyl substituent to contain from 1 to about 12 and even more typically from about 1 to about 4 carbon atoms and/or for the average number of carbon atoms per alkyl substituent to be not greater than about 2.

Other examples of substituents optionally present on a π-cyclopentadienyl ring in the radicals represented by Cp include various polymeric materials such as, for example, a polystyrene. In some embodiments it may be advantageous for such a polymeric material to have sufficient molecular weight that it is a solid (e.g., a polymeric resin) under the conditions of the process of this invention, thereby facilitating maintenance of the zirconium compound in a fixed position for ease of separation of the chlorinated acyl compound of the process disclosed herein.

Although this process may be carried out satisfactorily using zirconium compounds comprising π-indenyl or π-fluorenyl radicals, it is a preferred embodiment of the process which utilizes such a compound comprising two monocyclic-π-cyclopentadienyl radicals such as, for example, unsubstituted π-cyclopentadienyl or pentamethyl-π-cyclopentadienyl radicals.

The zirconium compounds employed in this invention also comprise a monovalent entity (herein designated X) that is essentially non-interfering, that is, which does not prevent displacement of the desired radical from the zirconium compound in the reaction of this invention. In referring to X as a monovalent entity, it is not meant that said entity must be a monovalent atom, but only that it is monovalently linked to the zirconium atom in a compound of the kind represented by formulae herein. Thus, X can be a monovalent atom such as halogen, a more complex entity such as an alkoxy (e.g., methoxy, ethoxy or the like) or phenoxy radical, or even a much bulkier entity such as a normally solid material (e.g., a polymeric material such as a polystyrene) which may advantageously anchor the zirconium compound in a fixed position for ease of product separation as referred to hereinbefore. Preferred among such monovalent entities are the low ($C_1$–$C_4$) alkoxy radicals and the halogens, with the halogens being more preferred. Chlorine and bromine are generally preferred for economic reasons, and chlorine is normally most preferred.

The zirconium compounds which are subjected to chlorination in the process of this invention also comprise a group, designated as R above, which is alkyl or cycloalkyl, either of which may be substituted or unsubstituted. Illustrative examples of unsubstituted alkyl and cycloalkyl groups are ethyl, n-propyl, n-butyl, isobutyl, n-pentyl, isopentyl, n-hexyl, n-octyl, n-undecyl, n-dodecyl, cyclopropyl, cyclobutyl, cyclopentyl, cyclohexyl, cyclooctyl and even larger cyclic alkyls. Examples of substituted alkyl and cycloalkyl groups are variations of the aforementioned groups having halo-, phenoxy, alkoxy, aryl, cycloalkyl or the like substituents. Those skilled in the art will recognize that the wide variety of substitution which is possible in the R group is limited only by the condition that the sterically least hindered position of R be bonded to the C=O in formula (1) above. In other words, there cannot be substitution in R which would result in R having a position of less steric hindrance than the position which is bonded to the C=O in formula (1).

In preferred embodiments of this invention R is unsubstituted alkyl (straight-chain or branched) or unsubstituted cycloalkyl. It is also preferred that R contain from 3 to 30 carbon atoms. Most preferred is that R be unsubstituted alkyl (straight-chain or branched) containing from 3 to 30 carbon atoms.

The zirconium compounds which are subjected to chlorination in the process of this invention can be prepared using procedures of the kind identified in the aforecited article by Schwartz and Labinger (it being possible to substitute the aforementioned non-interfering monovalent entities for chlorine and substituted π-cyclopentadienyl for unsubstituted π-cyclopentadienyl radicals) or by other procedures described in the art. For example, these compounds can be prepared by reacting a zirconium salt having the formula $ZrX_4$ wherein X has the aforedescribed significance (e.g., a zirconium tetrahalide, tetra-alkoxide or the like) with an appropriate π-cyclopentadienyl sodium salt, which can be made by reacting sodium hydride with an alkyl-π-cyclopentadiene having such additional ring substituents as are desired. The resulting $Cp_2ZrX_2$ compound can then be converted to the corresponding monohydride ($Cp_2ZrXH$), then to its corresponding alkyl derivative ($Cp_2ZrXR$), and then to the corresponding acyl derivative ($Cp_2ZrXCOR$) by reaction with carbon monoxide, again by procedure of the kind identified in that article by Schwartz and Labinger.

The following example illustrates the preparation of a zirconium compound of the type employed in the chlorination process of this invention. In this and all subsequent examples the term "millimole" and "Vapor Phase Chromatography" are abbreviated "mmole" and "VPC," respectively.

EXAMPLE I

Preparation of an Acylzirconium Compound

A mixture of 1.105 grams (4.24 mmole) of di(π-cyclopentadienyl)zirconium chlorohydride ($Cp_2ZrClH$), 3.55 grams of a 19.98 percent by weight solution of 1-dodecane in n-tetradecane (4.21 mmole of 1-dodecene) and 25 milliliters of benzene was stirred and refluxed for approximately 15 minutes in a flask under an argon atmosphere at ambient pressure. By analysis of an aliquot of the solution it was determined that the resulting purple solution contained 3.03 mmole of di(π-cyclopentadienyl)(1-dodecyl)zirconium chloride ($Cp_2ZrCl(n\!-\!C_{12}\!-\!H_{25})$). The analysis consisted of brominating the aliquot with a 10 percent by weight solution of bromine in benzene followed by VPC analysis for $n\!-\!C_{12}H_{25}Br$.

Essentially all of the resulting purple solution (small aliquots were taken for analysis and other experiments) was then subjected to carbonylation by stirring in a pressure bottle at ambient temperature and an initial 6 atmospheres (absolute) of carbon monoxide. The pressure fell to approximately 5 atmospheres (absolute) over a 20 minute period and then remained constant for 4 hours. Solid impurities were allowed to settle and the supernatant liquid comprising di(π-cyclopentadienyl) (1-oxo-tridecyl) zirconium chloride

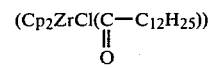

was removed for chlorination (as described in Example II).

This invention provides a process for chlorinating zirconium compounds of formula (1) above by contacting the compound with chlorine in the substantial absence of light. The acyl group is cleaved from the zirconium compound and replaced with a chlorine atom. Another chlorine atom attaches to the cleaved acyl group at the position which was bonded to the zirconium. Thus, the resultant mixture of the chlorination reaction in the process of this invention comprises a zirconium chloride and an acyl chloride, and it is usually desirable to then recover these materials.

The process of this invention is particularly useful in the preparation of acyl chlorides from acyl zirconium compounds which have been prepared by reacting a zirconium halohydride with an internal olefin according to above-described procedures. This sequence of reactions thus provides for the preparation of acyl chlorides from internal olefins.

Gaseous or liquid chlorine can be employed in the process of this invention, and gaseous chlorine is preferred. A mole of chlorine is required for each mole of the zirconium compound to be chlorinated. It is preferred to carry out the reaction with a slight stoichiometric excess of chlorine to assure completion of the reaction. It may even be desirable to use a larger excess of chlorine, for instance, if the reaction mixture contains impurities which react with the chlorine. Partial chlorination will result if less than a stoichiometric amount of chlorine is employed.

In the process of this invention, it has surprisingly been found that high yields of the acyl chloride are obtained by carrying out the reaction in the substantial absence of light. The same reaction carried out in the presence of ordinary room light produces a substantial amount of undesirable by-products and a much lower yield of the acyl chloride. The "substantial absence of light" herein means the absence of light of an amount or type which causes the formation of a significant amount of undesirable products in the chlorination reaction of the process of this invention. Thus, it is possible that exposure to very small amounts of ordinary room light would not substantially interfere with the reaction desired in the process of this invention. Also, it is possible that certain wavelength light may not affect the process of this invention, but any such light would probably have to be in a wavelength region lower than the ultraviolet region. It is preferred to carry out the process of this invention in the dark, that is, essentially devoid of light.

The reaction time, temperature and pressure are not critical in the process of this invention. The reaction is exothermic and essentially instantaneous under ambient conditions. It is possible that side reactions may result at extremely high temperatures and it is therefore preferred to react at a temperature of about 0° to about 100° C. Even more preferred is a temperature of about 30° to about 50° C. Since the reaction is exothermic it may be desirable to use a means of cooling to control the reaction temperature.

The reaction is typically carried out in the presence of a solvent. Any solvent which does not readily react with chlorine is acceptable. Benzene is particularly advantageous and preferred since the zirconium compounds are often prepared in this solvent. Also preferred are other aromatic hydrocarbons which do not readily react with chlorine (e.g., toluene and the xylenes), and halogenated hydrocarbons such as chlorobenzene and dichloroethane.

After carrying out the chlorination reaction of this invention, the resulting products, that is, the chlorinated zirconium compound and acyl chloride, can be recovered by conventional means such as distillation and filtration. One skilled in the art will recognize that various conditions for such recovery are possible so long as the conditions do not result in decomposition of the products.

Alternatively, it may be desirable to take a crude form of either product and carry out reactions known in the art to convert the product to a derivative, and then carry out recovery steps, again by methods known in the art.

The following examples are given to illustrate the invention in detail. It is to be understood that the specific details in these examples are not to be construed as limiting the scope of the invention.

EXAMPLE II

Chlorination in the Dark

The solution prepared in Example I comprising di($\pi$-cyclopentadienyl)(1-oxo-tridecyl) zirconium chloride

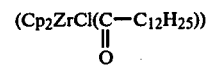

was placed in a flask which was filled with argon and surrounded by aluminum foil to keep out light. The starting temperature and pressure in the flask were ambient. The flask was then placed in an ice bath and the aliquot was treated with chlorine by injecting approximately a 10 percent molar excess (based on the alkylzirconium determined to be present in Example I) of chlorine gas into the flask using a syringe while stirring the mixture. Solids (comprising $Cp_2ZrCl_2$) were removed by centrifugation and washed with benzene. The combined washings and decanted liquor containing the n-tridecanoyl chloride was then treated with excess methanol with cooling the convert this acid chloride to methyl tridecanoate. VPC analysis of the resulting solution showed the formation of methyl tridecanoate in 96 percent yield based on the 1-dodecyl zirconium determined to be present in Example I. This result confirms that there was essentially complete conversion of the 1-dodecyl zirconium to the corresponding acylzirconium in the carbonylation reaction of Example I and indicates that the yield for the chlorination reaction of this Example was at least 96 percent.

EXAMPLE III

Preparation of n-tridecanoyl Chloride From a $C_{12}$ Hydrocarbon Mix

A dilute $C_{12}$ hydrocarbon mix was produced by catalytic dehydrogenation of straight-chain $C_{12}$ paraffin. A mixture of 89.29 grams of this $C_{12}$ hydrocarbon mix (63.07 mmole of $C_{12}$ mono-olefin), 29.40 grams (114.0 mmole) of di($\pi$-cyclopentadienyl)zirconium chlorohydride ($Cp_2ZrClH$), and 100 milliliters of tetrahydrofuran (THF) was stirred in a flask filled with argon and heated to reflux at ambient pressure for 30 minutes. The amount of di($\pi$-cyclopentadienyl)(n-dodecyl)zirconium chloride ($Cp_2ZrCl(n—C_{12}H_{25})$) present in the resulting solution was determined to be 33.06 moles by analysis which consisted of iodination of a sample of the resulting solution followed by VPC analysis for $n—C_{12}H_{25}I$.

The resulting solution was then vacuum distilled at room temperature to remove the THF solvent. By continued vacuum distillation (30° C. and 0.01 mm. Hg. absolute pressure) overnight, the majority of residual hydrocarbon mix was then removed. The pot residue containing the alkylzirconium compound was taken up in benzene and centrifuged. The liquid was transferred to a pressure tube. The solid was washed repeatedly with benzene (approximately 150 milliliters total benzene used) and the washings were combined with the liquid in the pressure tube.

The benzene solution of the alkylzirconium compound was then carbonylated by stirring overnight at room temperature under 4.4 atmospheres (absolute) of C=O. The resulting solution comprising the acylzirconium compound was then chlorinated in the dark by the addition of chlorine gas to the reaction vessel which was immersed in an ice bath and surrounded by aluminum foil to keep out light. A total of 4.71 grams of chlorine was added and a positive pressure registered on the reactor. The reaction was completed within one hour. The resulting solid plus liquid reaction mixture was separated by centrifugation and the liquid product comprising the desired n-tridecanoyl chloride was added to 75 milliliters of cold methanol. The solid was washed with benzene and the washings were added to the methanol mixture. The methanol and benzene was then removed from the methanolyzed reaction product by room temperature vacuum distillation. The residue of liquid and solid was filtered into a distillation pot using pentane to wash. The pentane was evaporated from the mixture and the residue was vacuum distilled (0.03 mm Hg.). There was obtained 6.89 grams of 93 percent pure (VPC) methyl n-tridecanoate showing satisfactory infrared (ir) and nuclear magnetic resonance (nmr) spectra. This corresponds to a yield of 85 percent based on the alkyl zirconium determined to be present prior to the carbonylation reaction and thus the yield of the desired n-tridecanoyl chloride from the chlorination reaction was at least 85 percent.

Although the invention has been described with respect to certain specific embodiments, it is not so limited, and it is to be understood that variations and modifications thereof may be made without departing from the spirit of the invention.

The embodiments of this invention in which an exclusive property or privilege is claimed are defined as follows:

1. A process which comprises contacting a compound of the formula $$\begin{array}{c} Cp \\ \diagdown \\ \diagup \\ Cp \end{array} Zr \begin{array}{c} X \\ \diagdown \\ \diagup \\ C-R \\ \parallel \\ O \end{array}$$

wherein
Cp is a π-cyclopentadienyl radical and each Cp can be the same or different,
X is an essentially non-interfering monovalent entity, and
R is alkyl or cycloalkyl, either of which may be unsubstituted or substituted, provided that the sterically least hindered position of R is bonded to C=O in the formula,
with chlorine in the substantial absence of light to form $$\begin{array}{c} Cp \\ \diagdown \\ \diagup \\ Cp \end{array} Zr \begin{array}{c} X \\ \diagdown \\ \diagup \\ Cl \end{array}$$

and $$Cl-\underset{\underset{O}{\parallel}}{C}-R.$$

2. A process according to claim 1 wherein R contains from 3 to 30 carbon atoms.

3. A process according to claim 1 wherein X is a halogen.

4. A process according to claim 3 wherein X is bromine or chlorine.

5. A process according to claim 4 wherein X is chlorine.

6. A process according to claim 1 wherein the Cp radicals are mono-cyclic-π-cyclopentadienyl radicals.

7. A process which comprises contacting a compound of the formula $$\begin{array}{c} Cp \\ \diagdown \\ \diagup \\ Cp \end{array} Zr \begin{array}{c} Cl \\ \diagdown \\ \diagup \\ C-R \\ \parallel \\ O \end{array}$$

wherein
Cp is a mono-cyclic-π-cyclopentadienyl radical and each Cp can be the same or different, and
R is alkyl or cycloalkyl, either of which may be unsubstituted or substituted, provided that the sterically least hindered position of R is bonded to C=O in the formula,
with chlorine in the substantial absence of light to form $$\begin{array}{c} Cp \\ \diagdown \\ \diagup \\ Cp \end{array} Zr \begin{array}{c} Cl \\ \diagdown \\ \diagup \\ Cl \end{array} \quad \text{and} \quad Cl-\underset{\underset{O}{\parallel}}{C}-R.$$

8. A process according to claim 7 wherein R contains from 3 to 30 carbon atoms.

9. A process according to claim 8 wherein R is unsubstituted or substituted alkyl.

10. A process according to claim 9 wherein R is unsubstituted alkyl.

* * * * *